(12) United States Patent
Sand et al.

(10) Patent No.: US 8,936,766 B2
(45) Date of Patent: Jan. 20, 2015

(54) DEVICE AND METHOD FOR DELIVERING MECHANICALLY RELEASED CELLS FROM LIPOSUCTION ASPIRATES

(75) Inventors: Ted Sand, Austin, TX (US); Kevin Dunworth, Dripping Springs, TX (US); Greg Forman, Earlysville, VA (US)

(73) Assignee: SpineSmith Partners, L.P., Austin, TX (US)

( * ) Notice: Subject to any disclaimer, the term of this patent is extended or adjusted under 35 U.S.C. 154(b) by 26 days.

(21) Appl. No.: 13/200,910

(22) Filed: Oct. 4, 2011

(65) Prior Publication Data

US 2012/0264213 A1    Oct. 18, 2012

Related U.S. Application Data

(60) Provisional application No. 61/404,462, filed on Oct. 4, 2010.

(51) Int. Cl.
*B01D 21/00* (2006.01)
*C12M 1/33* (2006.01)
*C12M 1/00* (2006.01)

(52) U.S. Cl.
CPC ............... *C12M 45/02* (2013.01); *C12M 47/04* (2013.01)
USPC ........ 422/527; 435/262; 435/366; 435/285.1; 435/325; 494/67; 494/40; 494/60

(58) Field of Classification Search
USPC ............... 494/67; 210/170.02; 435/262, 366, 435/285.1, 325; 422/527
See application file for complete search history.

(56) References Cited

U.S. PATENT DOCUMENTS

| | | | | |
|---|---|---|---|---|
| 5,156,586 | A | * | 10/1992 | Fitch et al. ....................... 494/67 |
| 5,256,376 | A | | 10/1993 | Callan et al. .................... 422/102 |
| 5,478,744 | A | | 12/1995 | Sanford et al. ............. 435/285.1 |
| 7,429,488 | B2 | * | 9/2008 | Fraser et al. ................... 435/366 |
| 2007/0264704 | A1 | * | 11/2007 | Van Toever ................... 435/262 |
| 2008/0243028 | A1 | | 10/2008 | Howard et al. ............... 600/565 |
| 2009/0192498 | A1 | * | 7/2009 | Andrew et al. ............... 604/542 |

OTHER PUBLICATIONS

International Patent Application No. PCT/US2011/001706, "International Search Report dated Jan. 13, 2012," International Filing Date Oct. 4, 2011.

* cited by examiner

*Primary Examiner* — Sally Merkling
(74) *Attorney, Agent, or Firm* — Winstead PC

(57) ABSTRACT

A lipoaspirate collection device to aid in the collection and processing of human tissue and fluid obtained during liposuction for use in point-of-care cell therapy. The collection device includes a collection body and a collection cap. The collection cap may have a fluid port, a lipoaspirate port, a vacuum port, and a relief valve. Within the central cavity of the collection device, a cone shaped may be positioned such that the apex of the cone is positioned underneath the lipoaspirate inlet through which the lipoaspirate fluid and tissue are introduced.

7 Claims, 1 Drawing Sheet

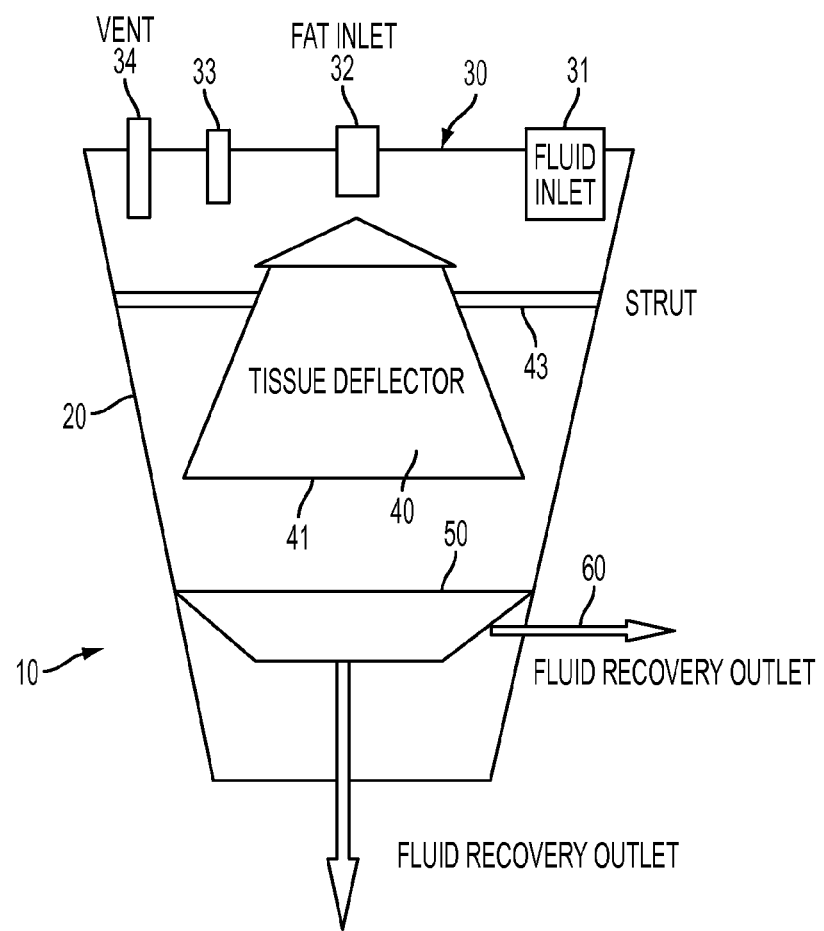

DEVICE AND METHOD FOR DELIVERING MECHANICALLY RELEASED CELLS FROM LIPOSUCTION ASPIRATES

This application claims priority to U.S. provisional application 61/404,462, filed Oct. 4, 2010, incorporated in its entirety herein by reference.

FIELD OF THE INVENTION

The invention herein relates generally to a device and method to obtain mechanically released adipose derived progenitor cells for use in point of care therapeutic applications.

BACKGROUND OF THE INVENTION

Collection of adipose tissue through the application of liposuction methods is a common practice (Condé-Green, 2009). The procedure is easily performed in most cases, has a low morbidity rate, and results in the collection of large volumes of adipose tissue (Katz and Maiwald, 2005). Zuk, et al. (2001) was one of the first groups to demonstrate the presence of "stem" cells in adipose tissue collected via lipoaspiration. Their results have been confirmed in subsequent publications (e.g., Yoshimura, et al., 2006). Due to the presence of regenerative cells in the fat tissue, there has been growing interest in using tissue collected during liposuction for body contouring, facial/body enhancement and recontouring in patients suffering from soft tissue atrophy (Condé-Green, 2009). There also has been a growing interest in using the cells isolated from fat tissue for regenerative cell therapy in a variety of pathologies, including repair of orthopedic tissue injuries (Tapp, et al., 2009).

A number of publications demonstrate how lipoaspirates may be non-enzymatically processed to extract adipose-derived stem cells (ASCs) and progenitor cells from adipose tissue. It is apparent that viable cells can be obtained from mechanical dissociation of the fatty portion of lipoaspirate when collected following either centrifugation or washing of the fatty tissue, but non-enzymatic processing yields fewer cells per mL of lipoaspirate (Baptista, et al., 2009; Yoshimura, et al., 2006).

Collagenase digestion of the adipose tissue is the most common practice for enzymatically digesting lipoaspirates. Enzymatic processing of adipose tissue may yield a higher number of cells than current non-enzymatic processing methods; however, enzymatic processing results in more difficult processing, slower return of cells to the patient, higher cost to provide the cells, and more stringent FDA regulation. Many processing methods, both non-enzymatic and enzymatic, also ignore the fact that a significant amount of progenitor cells can be obtained from the lipoaspirate fluid alone with minimal processing.

SUMMARY OF THE INVENTION

The disclosed device and method provide a solution to the problems and disadvantages described above by providing a device and method for facilitating the collection and processing of adipose tissue and fluid obtained during liposuction. The lipoaspirate extraction system of this invention mechanically stresses adipose tissue that will be infiltrated and removed. Mechanical stress might induce the migration of useful cell types into the area, thereby enhancing their concentration and improving the yield of useful cell types, such as progenitor cells. Use of a vacuum to suction the area of tissue to be probed will serve to limit the degree of trauma being introduced to the patient that can occur in liposuction procedures. The system also limits the probing of the adipose tissue to defined locations and geometries. Ports may also be designed to further control the depth of penetration during each probe event. More gentle collection conditions should provide for a higher number of viable cells collected compared to standard liposuction practice.

In one respect, this invention is a device to facilitate the collection and processing of mechanically released adipose derived progenitor and/or stem cells from fluid obtained during liposuction, comprising: a collection body having an upper collection body cap wherein the collection body cap has a fluid port for introducing fluids, a lipoaspirate port through which lipoaspirate is introduced, a vacuum port, wherein the collection body has a central cavity in which is positioned a cone shaped deflector such that the apex of the cone is positioned pointed toward the upper collection body cap and such that the apex is positioned underneath the lipoaspirate inlet.

The cone may include a series of holes positioned near the apex of the cone to prevent an air lock, wherein the holes may optionally be covered by a disc to deflect tissue away from the holes. In one embodiment, the collection body has a substantially cylindrical shape. The device may include a debris capturing trough, constructed with various micro-texturing patterns to facilitate the retention of debris and circumferentially disposed along the inner wall of the collection body beneath the circular base of the defector; the trough optionally including a lip to help capture any sinking debris and the collection body further including a pit beneath the debris capturing trough to collect any additional sinking debris. The device may further include at least one fluid recovery outlet to remove fluid from the collection body, and optionally an additional filter placed adjacent to the fluid recovery outlet to prevent any additional debris from leaving the collection body. The device may include needleless entry technology, so that it can be maintained in a sterile manner, but is readily accessible for connecting to a tube for removing the fluid. The device may be arranged such that the fluid recovery outlet is laterally positioned above the pit, so that only fluid exits through the fluid recovery outlet. The device can be formed from stainless steel and plastic materials.

In another broad respect, the invention is a lipoaspirate extraction system constructed from a variety of materials, including stainless steel and plastic, used to extract lipoaspirate materials from a patient in a surgical field comprising: an adipose disruption component, an infiltration component, and, an extraction component. The system may include a means to mechanically disrupt adipose tissue using any number of mechanisms, including, but not limited to, a vacuum, ultrasound, massage, fluid jets, or mechanical rollers, wherein the mechanical means can cycled on and off as appropriate. The adipose disruption component may include two devices; one to provide mechanical stress and a second, discrete device that is used to apply a vacuum to maintain the position of the adipose disruption component. The infiltration component may include at least one infiltration port through which a cannula or alternative device may be introduced to deliver infiltration fluids between the dermis and muscle, said fluids comprising, but are not limited to, physiologically compatible fluids like Lactated Ringer's, saline, Phosphate Buffered Saline, all of which can be obtained as sterile and non-pyrogenic fluids, and said fluids may additionally contain other agents, including, but not limited to, epinephrine and lidocaine. The extraction component may include vacuum capabilities to maintain the position of the extraction component, through which a specially designed extraction probe or alternative device may be introduced to extract lipoaspirate material.

In another broad respect the invention is a method of using a device to extract and collect mechanically released adipose derived progenitor cells wherein: lipoaspirate material will enter a collection device through an entry port, said collection device will be pre-filled with a fluid to facilitate separation between the fluid, fat tissue, and debris, and, sinking debris will flow down the outer surface of the deflector and settle into a trough or pit where the lipoaspirate fluid can then be removed through fluid recovery ports. The lipoaspirate extraction system may be used either simultaneously or sequentially with a lipoaspirate collection mechanism and, the lipoaspirate extraction system can be used to promote the mechanical release of cells from the tissue matrix in-vivo, at the collection site, before, and/or during the actual extraction and collection of adipose tissue and fluids.

In another broad respect, the invention is a method of using a device to extract and collect mechanically released adipose derived progenitor cells, comprising: Introducing lipoaspirate material will into a collection device through an entry port, said collection device being pre-filled with a fluid to facilitate separation between the fluid, fat tissue, and debris, wherein the collection device has a central cavity in which is positioned a cone shaped deflector such that the apex of the cone is positioned pointed toward the upper collection body cap and such that the apex is positioned underneath the lipoaspirate inlet, and allowing debris to flow down the outer surface of the deflector and settle into a trough where the lipoaspirate fluid can then be removed through fluid recovery ports.

BRIEF DESCRIPTION OF THE DRAWINGS

FIG. 1 shows a lipoaspirate device 10 of this invention.

DETAILED DESCRIPTION OF THE INVENTION

Lipoaspirate Collection Device

The lipoaspirate collection device is designed to aid in the collection and processing of human tissue and fluid obtained during liposuction for use in point-of-care cell therapy. The collection device decants fluid from lipoaspirate materials, eliminating floating and sinking debris for quick and easy evacuation of fluid and cells from the container. The collection device may also be used to rinse the lipoaspirate material to extract more progenitor cells.

In one embodiment, as shown in FIG. 1, the collection device 10 includes a collection body 20 and a collection cap 30. The collection cap 30 may have a fluid port 31 for introducing fluids, a lipoaspirate port 32 through which lipoaspirate is introduced, a vacuum port 33, and a relief valve port 34. Each port in the collection cap 20 may include a tight fitting cap for sealing each port. These tight fitting caps may be connected to the collection cap 20 in a manner that keeps the tight fitting caps in close proximity to their respective ports.

The collection body may take a substantially cylindrical shape. Within the central cavity of the collection device, a cone shaped deflector 40 may be positioned such that the apex of the cone is positioned underneath the lipoaspirate inlet through which the lipoaspirate fluid and tissue are introduced. The circular base 41 of the deflector is large enough to nearly reach the inner wall of the collection device. A series of small holes may be positioned near the apex of the cone to prevent an air lock. The holes may be covered by a disc to deflect tissue away from the holes. This disc will be attached to the outer surface of the deflector at its apex. The deflector itself may be attached to the inner wall of the collection device via the placement of a plurality of struts 43 designed to maintain the position and orientation of the deflector within the cavity. A debris capturing trough 50 may be circumferentially disposed along the inner wall of the collection body, just underneath the circular base of the defector. The trough may include a lip to help capture any sinking debris. The deflector and trough may also be constructed with various micro-texturing patterns to facilitate the retention of debris. The collection body also includes at least one fluid recovery outlet 60 to remove fluid from the collection body. An additional filter may be placed adjacent to the fluid recovery outlet to prevent any additional debris from leaving the collection body. The fluid recovery outlet may incorporate needleless entry technology, so that it can be maintained in a sterile manner, but is readily accessible for connecting to a tube for removing the fluid. The collection device may also include a wide base to maintain the collection device in an upright position.

In an alternative embodiment, the collection device may include a pit at the bottom of the collection body to collect any sinking debris. The fluid recovery outlet is laterally positioned above the pit to so that only fluid exits through the fluid recovery outlet.

Lipoaspirate Extraction System

In another embodiment, a lipoaspirate extraction system is used to extract lipoaspirate materials from a patient in a surgical field. The lipoaspirate device may be constructed from a variety of materials, including stainless steel and plastic. Stainless steel construction allows the extraction system to be repeatedly autoclaved without alteration of the physical integrity of the device. On the other hand, the extraction system can be made out of plastic, rendering it disposable. The lipoaspirate extraction system comprises an adipose disruption component, an infiltration component, and an extraction component. The lipoaspirate extraction system may be constructed such that the adipose disruption component, infiltration component, and extraction components are all incorporated into one device or separate devices.

The adipose disruption component mechanically disrupts adipose tissue using any number of mechanisms, including, but not limited to, a vacuum, ultrasound, fluid jets, or mechanical rollers. For example, the lipoaspirate extraction system may be a vacuum based system. The vacuum housing may take a circular, elliptical, or alternative shape depending on the site on which the liposuction is to be performed. The variation and degree of suction can be controlled by standard means known in the art. Alternatively, if mechanical stress is applied through means such as massage or ultrasonic energy, it is contemplated that the vacuum can be cycled on and off as appropriate. In this regard, it may be appropriate to have two devices in use, one to provide mechanical stress and a second, discrete device that is used to apply a vacuum to maintain the position of the adipose disruption component. It also might be appropriate to design a single device that performs both functions.

The infiltration component includes at least one infiltration port through which a cannula or alternative device may be introduced to deliver infiltration fluids between the dermis and muscle. Candidate fluids include, but are not limited to, physiologically compatible fluids like Lactated Ringer's, saline, or Phosphate Buffered Saline, all of which can be obtained as sterile and non-pyrogenic fluids. The infiltration fluid may or may not contain other agents, including, but are not limited to, epinephrine and lidocaine. Each infiltration port may include a septum, which can be separately sterilized and aseptically affixed to each port. Assembly of such ports and fixtures also could occur prior to sterilization of the device. The ports may be designed in such a way that it is possible to insert a cannula or other probe from the outside of the device into the device's lumen without breaking the vacuum. The infiltration component may also include vacuum capabilities to maintain the position of the infiltration component. Depending on the stability of the device relative to maintaining a seal and therefore the vacuum, it may be possible to close the vacuum port by turning a valve. Alternatively, the vacuum may be applied continuously during the procedure by maintaining connection to an appropriate source of vacuum.

The extraction component may include vacuum capabilities to maintain the position of the extraction component. The extraction component includes at least one extraction port through which a specially designed extraction probe or alternative device may be introduced to extract lipoaspirate material. Each extraction port may include a septum, which can be separately sterilized and aseptically affixed to each port. Assembly of such ports and fixtures also could occur prior to sterilization of the device. The ports may be designed in such a way that it is possible to insert a cannula or other probe from the outside of the device into the device's lumen without breaking the vacuum. The extraction probe may include a flange along the probe body to limit insertion of the cannula through the extraction ports. The extraction probe may also be specially designed to limit extracted lipoaspirate material primarily to interstitial fluid.

The lipoaspirate extraction system and collection device may be used together or separately. Extracted lipoaspirate fluid may then be manually processed to concentrate ASCs and progenitor cells. These cells may then be delivered to the patient for use in regenerative cells therapies.

One method of using the collection device is in conjunction with standard liposuction techniques, which are used to remove lipoaspirate materials from the surgical field. The lipoaspirate material will enter the collection container through the lipoaspirate port. The collection device will be pre-filled with a fluid to facilitate separation between the fluid, fat tissue, and debris. Sinking debris will flow down the outer surface of the deflector and settle in the trough. Lipoaspirate fluid can then be removed through the fluid recovery ports.

In an alternative method, the lipoaspirate extraction system may be used in conjunction with any lipoaspirate collection mechanism known in the art. The lipoaspirate extraction system can be used either simultaneously or sequentially with a lipoaspirate collection mechanism. The lipoaspirate extraction system can be used to promote the mechanical release of cells from the tissue matrix in-vivo, at the collection site, before, and/or during the actual extraction and collection of adipose tissue and fluids. The system mechanically stresses an area of adipose tissue to induce the migration of useful cell types into the area, thereby enhancing their concentration and improving the yield of useful cell types, such as progenitor cells. Thus, it may be beneficial to apply the mechanical stress before and/or during the infiltration of fluid and then to continue to apply the stress after the infiltration has been completed. It is contemplated that there could be a delay in the initiation of a subsequent step in order to maximize the yield of cells at the conclusion of the process. For example, it might be appropriate to mechanically stress the collection site one or more days in advance of the target date for collection. It further is contemplated that there might be periods of "incubation" during which the tissue is not mechanically stressed and allowed to "rest" before applying more stress. An extraction probe may be delivered through specific ports to remove primarily interstitial fluid from the adipose tissue. Lipoaspirate materials are extracted into a collection device.

Although illustrative embodiments have been shown and described, a wide range of modifications, changes, and substitutions are contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

REFERENCES

Baptista, L S, do Amaral, R J F C, Carias, R B V, Aniceto, M, Claudio-da-Silva, C and R Borojevic. 2009. An alternative method for the isolation of mesenchymal stromal cells derived from lipoaspirate samples. *Cytotherapy.* 11(6):706-715.

Condé-Green, A, Gontiljo de Amorim, N F and I Pitanguy. 2009. Influence of decantation, washing and centrifugation on adipocyte and mesenchymal stem cell content of aspirated adipose tissue: a comparative study. *J. Plast. Reconstr. Aesthet. Surg.* doi:10.11016/j.bjps.2009.07.018

Katz, B E and D C Maiwald. 2006. Power Liposuction. Dermatol. Clin. 23:383-391

Tapp, H, Hanley Jr., E N, Patt, J C and H E Gruber. 2009. Adipose-Derived Stem Cells: Characterization and Current Applications in Orthopaedic Tissue Repair. *Exp. Biol. Med.* 234:1-9

Yoshimura, K, Shigeura, T, Matsumoto, D, Sato, T, Takaki, Y, Aiba-Kojima, E, Sat, K, Inoue, K, Nagase, T, Koshima, I and K Gonda. 2006. Characterization of Freshly Isolated and Cultured Cells Derived from the Fatty and Fluid Portions of Liposuction Aspiates. *J. Cell. Physiol.* 208:64-76

Zuk, P A, Zhu, M, Miuzuno, H, Huan, J, Futrell, J W, Katz, A J, Benhaim, P, Lorenz, H P and M H Hedrick. 2001. Multilineage Cells from Human Adipose Tissue: Implications for Cell-Based Therapies. *Tissue Eng.* 7(2):211-228

What is claimed is:

1. A device to facilitate the collection and processing of mechanically released adipose derived progenitor and/or stem cells from fluid obtained during liposuction, comprising:
    a collection body having an upper collection body cap wherein the collection body cap has a fluid port for introducing fluids, a lipoaspirate port through which lipoaspirate is introduced, a vacuum port, and a relief valve port, wherein the collection body has a central cavity in which is positioned a cone shaped deflector such that the apex of the cone is positioned pointed toward the upper collection body cap and such that the apex is positioned underneath the lipoaspirate inlet, and wherein the deflector is attached to the inner wall of the collection body via a plurality of struts that maintain the position and orientation of the deflector within the central cavity.

2. The device of claim 1, wherein the cone includes a series of holes positioned near the apex of the cone to prevent an air lock, wherein the holes may optionally be covered by a disc to deflect tissue away from the holes.

3. The device of claim 1 wherein the collection body has a substantially cylindrical shape.

4. The device of claim 2, further comprising:
    a debris capturing trough or pit, constructed with various micro-texturing patterns to facilitate the retention of debris and circumferentially disposed along the inner wall of the collection body beneath the circular base of the cone shaped deflector; the trough optionally including a lip to help capture any sinking debris and the collection body further including a pit beneath the debris capturing trough to collect any additional sinking debris.

5. The device of claim 2, further comprising:
at least one fluid recovery outlet to remove fluid from the collection body, and optionally an additional filter placed adjacent to the fluid recovery outlet to prevent any additional debris from leaving the collection body.

6. The device of claim 4 comprising:
needleless entry technology, so that it can be maintained in a sterile manner, but is readily accessible for connecting to a tube for removing the fluid.

7. The device of claim 4 wherein the fluid recovery outlet is laterally positioned above the pit of claim 3, so that only fluid exits through the fluid recovery outlet.

* * * * *